United States Patent [19]

Olivier et al.

[11] Patent Number: 4,749,675

[45] Date of Patent: Jun. 7, 1988

[54] CATALYSTS FOR THE SELECTIVE DIMERIZATION OF ETHYLENE OR PROPYLENE TO MONOOLEFINES, OF THE TYPE BASED ON NICKEL ON A SILICA SUPPORT, PROCESS FOR PREPARING IT AND DIMERIZATION PROCESS EMPLOYING IT

[75] Inventors: Danièle Olivier, Villecresnes; Feng X. Cai; Christine Lepetit, both of Paris; Maggy Kermarec, Fontenay Aux Roses, all of France

[73] Assignee: Centre National de la Recherche Scientifique (CNRS), Paris, France

[21] Appl. No.: 879,248

[22] Filed: Jun. 27, 1986

[30] Foreign Application Priority Data

Jul. 4, 1985 [FR] France ................ 85 10235

[51] Int. Cl.$^4$ ............ B01J 23/74; B01J 31/16; C07C 2/24
[52] U.S. Cl. ............ 502/337; 585/514; 585/527; 585/529; 585/531
[58] Field of Search ........ 502/162, 337; 585/514, 585/510, 527, 529, 531

[56] References Cited

U.S. PATENT DOCUMENTS

| | | | |
|---|---|---|---|
| 3,808,246 | 4/1974 | Fahay | 585/514 |
| 3,949,013 | 4/1976 | Yoo et al. | 585/513 |
| 4,000,211 | 12/1976 | Smith et al. | 585/511 |
| 4,115,468 | 9/1978 | Antonov et al. | 502/117 |
| 4,118,432 | 10/1978 | Kabanov et al. | 502/117 |
| 4,187,197 | 2/1980 | Kabanov et al. | 502/117 |
| 4,382,153 | 5/1983 | Beach et al. | 585/511 |
| 4,487,847 | 12/1984 | Knudsen | 502/155 |
| 4,520,122 | 5/1985 | Arena | 502/162 |
| 4,528,415 | 7/1985 | Knudsen | 585/514 |
| 4,594,447 | 6/1986 | Wilke et al. | 502/162 |

FOREIGN PATENT DOCUMENTS 0089895  9/1983  European Pat. Off. .
3027782  2/1982  Fed. Rep. of Germany ...... 502/162

*Primary Examiner*—Asok Pal
*Attorney, Agent, or Firm*—Pollock, Vande Sande & Priddy

[57] ABSTRACT

The present invention relates to a catalyst for the selective dimerization of ethylene or of propylene into monoolefines of the type based on nickel on a silica support whose active sites are complexes of the Ni$^+$ ion. This catalyst is characterized in that practically the whole of the nickel is present in the form of Ni$^+$ complexes co-ordinated with the oxygen of the surface of the silica support and whose co-ordination sphere comprises one or two trialkylphosphine ligands. The invention also relates to a process for the preparation of these catalysts and to a process of dimerization employing them.

23 Claims, 5 Drawing Sheets

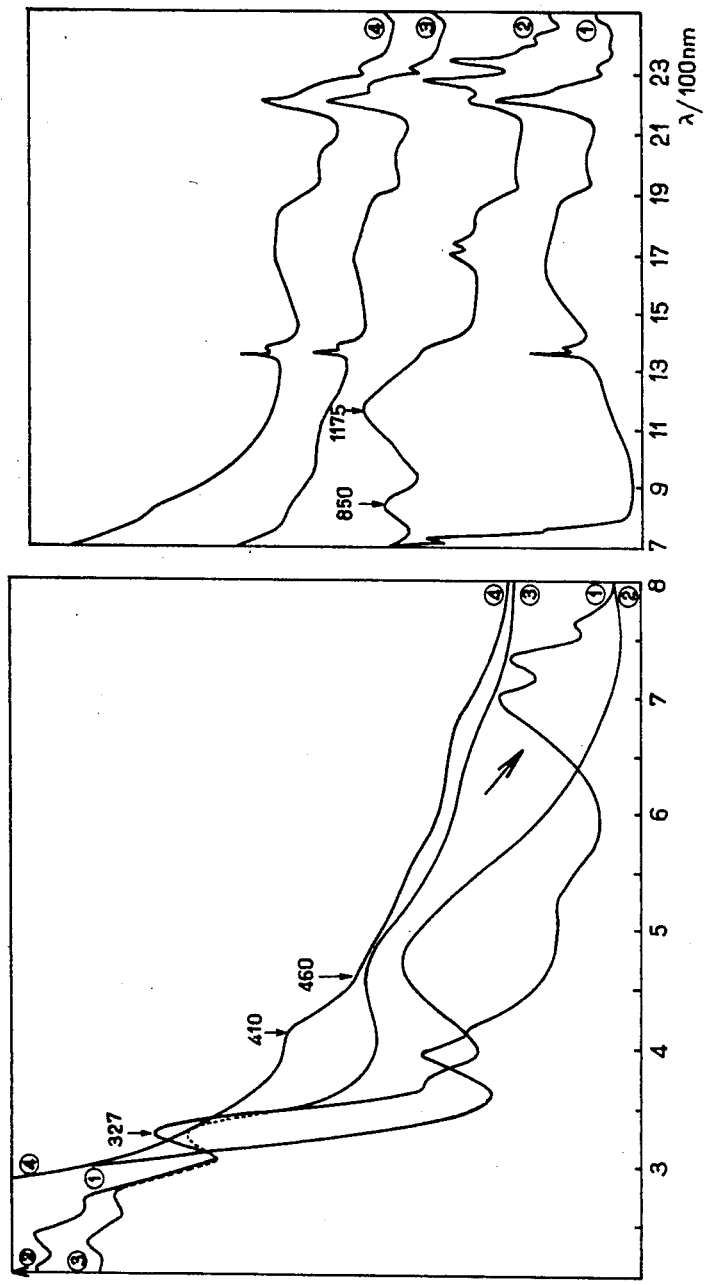
FIG_1

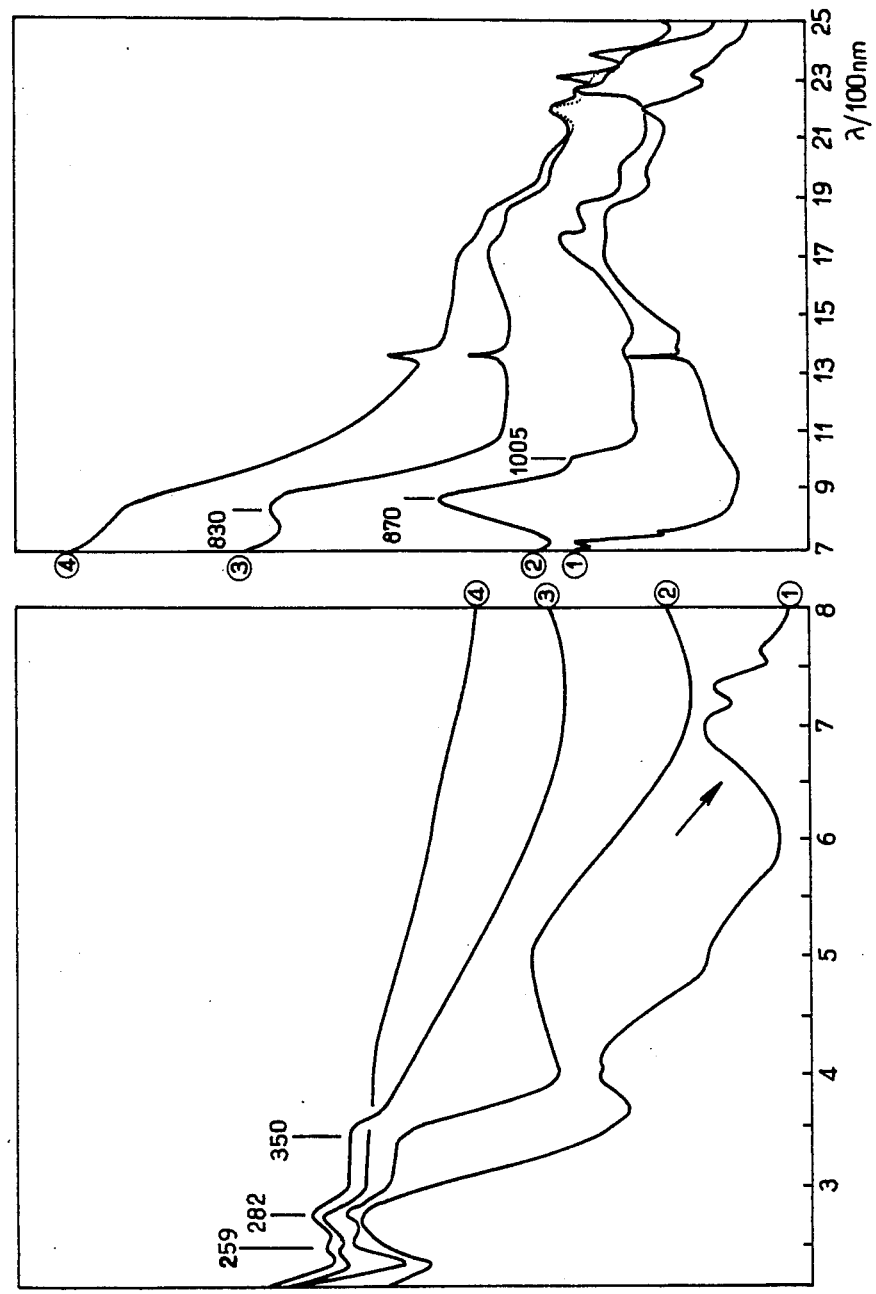
FIG_2

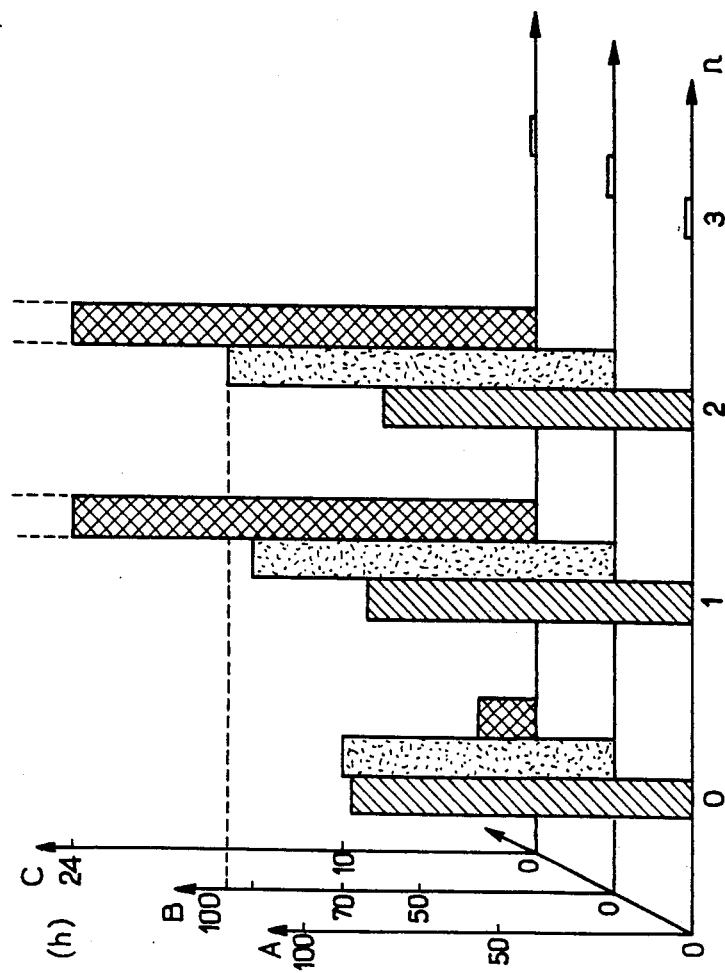
FIG_3

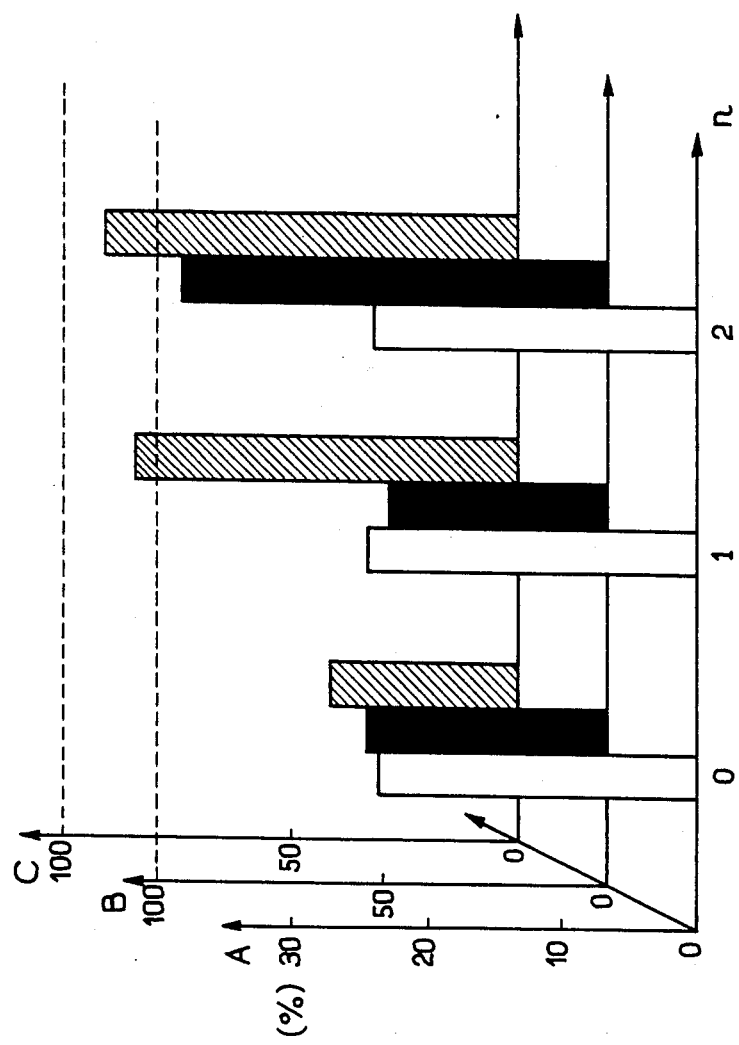
FIG_4

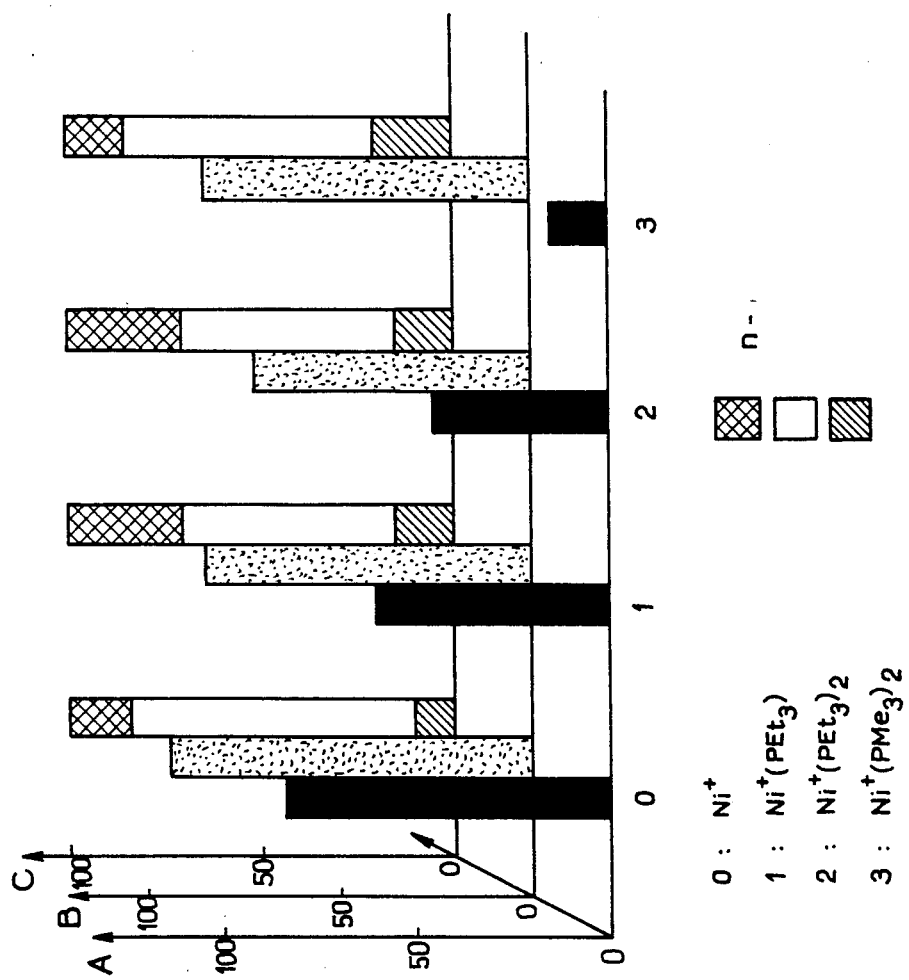
FIG_5

CATALYSTS FOR THE SELECTIVE DIMERIZATION OF ETHYLENE OR PROPYLENE TO MONOOLEFINES, OF THE TYPE BASED ON NICKEL ON A SILICA SUPPORT, PROCESS FOR PREPARING IT AND DIMERIZATION PROCESS EMPLOYING IT

BACKGROUND OF THE INVENTION

The present invention relates to a catalyst for the selective dimerisation of ethylene or of propylene into monoolefines, based on monovalent $Ni^+$ nickel on a silica support, as well as its preparation and dimerisation processes conducted in the presence of this catalyst.

In the prior art a certain number of heterogeneous catalysts based on nickel and on silica are already known, which are capable of dimerising olefines. As described by SOHN and OSAKI in the Journal of Catalysis 59, 303, 1979, these catalysts are mostly obtained by co-precipitation in a basic medium of a silica and a nickel salt followed by activation by heating between 100° and 600° C. These catalysts however only show weak activity, since the nickel is inside the silica in a form difficult to reduce.

Applicants have established that a more active catalyst can be obtained by employing a method of preparation enabling precisely the avoidance of passage through a nickel compound which is difficult to reduce.

This catalyst which is the subject of the application for European patent EP No. 008989555 in Applicant's name is characterised by the presence of precursors of sites of catalytic activity, constituted by complexes of monovalent nickel $Ni^+$ tri-co-ordinated with three atoms of oxygen of the surface of the silica support, this catalyst containing from about 0.01% to about 1% by dry weight of $Ni^+$, and monovalent nickel $Ni^+$ complexes can in particular comprise from one to three selective blocking ligands.

GENERAL DESCRIPTION OF THE INVENTION

According to the present invention there is provided an improvement in the catalysts of the prior art, namely selective dimerisation catalysts of ethylene or of propylene into monoolefines, of the type based on nickel on a silica support, whose active sites are complexes of the $Ni^+$ ion, characterised in that practically the whole of the nickel is present in the form of $Ni^+$ complexes co-ordinated with the oxygen of the surface of the silica support and whose co-ordination sphere comprises one or two trialkylphosphine ligands.

According to the present invention, practically all the nickel supported by the silica, present for about 1% to about 6% dry weight, is in active $Ni^+$ form.

The trialkylphosphine ligands which occupy, to the number of 1 or 2 according to the invention, the $Ni^+$ co-ordination sphere, are preferably trimethylphosphine ($PMe_3$) or triethylphosphine ($PEth_3$), although other selective ligands may be contemplated, for example triphenylphosphine or tricyclohexylphosphine.

The introduction into the co-ordination sphere of $Ni^+$ active species of a definite number (1 or 2) of trialkylphosphine ligands renders the catalyst according to the invention site selective for the dimerisation or ethylene or propylene into monoolefines. In addition, their activity is improved in intensity and in durability with respect to that of the caalysts of the prior art, and their selectivity is constant over time.

The catalysts according to the invention are characterised by their signals in EPR (Electronic Paramagnetic Resonance) spectroscopy and visible-UV spectroscopy. Thus, in particular, the catalyst according to the invention whose active sites are $Ni^+$ co-ordinated with two triethylphosphines ($Ni^+$ $(PEth_3)_2$) is characterised in EPR by values of about 2.32 ($g_{\parallel}$) and 2.083 ($g_{\perp}$) and 62 G ($A_{\perp 1}$) and 85 G ($A_{\perp 2}$) of the factors and hyperfine tensors and in visible-UV by transitions at 465 nm and 330 nm.

The catalyst according to the invention whose active sites are $Ni^+$ complexes co-ordinated with two trimethylphosphines ($Ni^+(PMe_3)_2$ is characterised in EPR by values of about 2.26 ($g_{\parallel}$) and 2.077 ($g_{\perp}$) and 60 G ($A_{\perp 1}$) and 75 G ($A_{\perp 2}$) factors and hyperfine tensors, and in visible-UV by transitions at 450 nm and 327 nm.

The catalyst according to the invention whose active sites are complexes of $Ni^+$ co-ordinated with a triethylphosphine ($Ni^+(PEth_3)$) is characterised in EPR by values of about 2.013 ($g_{\parallel}$) and 2.125 ($g_{\perp}$) and 70 G ($A_{\perp}$) factors and hyperfine tensors and in visible-UV by its transition at 400 nm.

The catalyst according to the invention whose active sites are $Ni^+$ complexes co-ordinated with a trimethylphosphine ($Ni^+(PMe_3)$) is characterised in EPR by values of about 2.015 ($g_{\parallel}$) and 2.120 ($g_{\perp}$) and 55 G ($A_{\perp}$) factors and hyperfine tensors, and in visible-UV by transitions at 400 nm.

The catalyst according to the invention whose active sites are complexes of $Ni^+$ co-ordinated with a ($Ni^+(P(C_6H_{11})_3)$ tricyclohexylphosphine is characterised in EPR by values of about 2.017 ($g_{\parallel}$) and 2.12 ($g_{\perp}$) and 55 G ($A_{\perp}$) factors and hyperfine tensors.

The present invention relates also to a process of manufacturing dimerisation caalysts according to the invention, characterised in that it comprises the following successive steps:

(a) treating silica with an aqueous solution of a compound generating monovalent cations, at a pH higher than about 10, so as to fix at least a part of said monovalent cations to the silica;

(b) treating the silica thus obtained with an aqueous solution of a divalent nickel salt and complexing agent of the nickel salt at a pH at least equal to about 8, so as to exchange said monovalent cations borne by the silica with divalent nickel cations;

(c) taking the thus modified silica to a temperature between 300° C. and 900° C., (d) treating the silica thus obtained with a trialkylphosphine or one of its precursors in excess until the production of $Ni^+$ complexes co-ordinated with four trialkylphosphine ligands, and (e) treating the resulting silica under vacuum at a suitable temperature and for an appropriate time to obtain active $Ni^+$ sites whose co-ordination sphere comprises at the most two trialkylphosphine ligands.

Other features and advantages of the present invention will be apparent from reading the detailed description of the following examples, and with reference to the accompanying drawings.

The dimerisation catalyst according to the invention is obtained by carrying out a process which is composed of five successive steps, presented below in detail.

(a) Fixation of monovalent cations to a silica

Silica is treated with an aqueous solution of a compound providing, in aqueous solution, monovalent cations particularly cations of alkali metals ammonium or quaternary ammonium, for example $NH_4^+$, $Na^+$, $Li^+$, K+ or NR4+ (R=monovalent hydrocarbon residue), at a pH higher than about 10, preferably between about 11 and 11.8.

Examples of compounds providing monovalent cations in solution, within the aforesaid pH range are soda, potash, ammonia and quaternary ammonium hydroxide, with or without additional salts, for example ammonium chloride, sodium nitrate, lithium chloride, ammonium acetate or a quaternary ammonium chloride or sulphate.

This fixation step is advantageously carried out at a temperature between 0° and about 80° C., preferably between about 20° and 60° C., by operating for example, in a vessel with stirring or by the circulation of the aqueous solution through a silica bed. The duration of the treatment may be extended, for example, from 3 hours to 3 days.

In the course of this fixation step, the pH must remain above 10 and preferably be comprised between about 11 and about 11.8, which may necessitate in certain cases the complementary addition of a base such as soda, potash or ammonia if an excessive drop in the pH is observed. To avoid this drawback, a preferred method consists of using the aqueous solution in sufficient amount and concentration for the pH not to drop by more than about 0.3 unit.

For this first treatment, the silica may be employed in any form, and particularly in the form of powder, beads or extruded elements.

(b) Competitive exchange of monovalent cations with the $Ni^{2+}$

The silica treated as indicated above and which contains monovalent cations is treated with an aqueous solution of a bivalent nickel salt and with a complexing agent for the nickel salt, at a pH of at least about 8, and preferably between about 9 and about 11.8. The basic complexing agent is advantageously ammonia or an amine, for example pyridine, monoethyl amine, diethyl amine, or trimethyl amine. The solution contains for example from about 0.001 to about 1 mole of nickel salt per liter, the concentration and the amount of solution being selected as a function of the number of monovalent ions that it is desired to exchange competitively. To provide an order of magnitude, 1 liter of this solution enables the treatment of between about 1 and about 100 g of silica. The duration of treatment is, for example, between about three hours and about three days, according to the desired competitive exchange ratio, and it may be done, for example, in a vessel with stirring or by circulation of the solution through a silica bed. The temperature of the competitive exchange is advantageously between about 0° and about 80° C. The modified silica thus obtained is separated from the aqueous phase and washed with water. It contains, for example, between about 0.01 and about 10% by dry weight of nickel.

It is preferable to limit the competitive exchange ratio of nickel to about 7% in order to avoid the formation of metallic nickel in the course of the subsequent reduction. Thus preferably 1 to 6% by weight of nickel is fixed to the silica.

(c) Thermal Pretreatment

The silica obtained in the course of the preceding step is then brought to a temperature between about 300° and about 900° C., preferably between about 500° and about 700° C. It is possible to operate under vacuum, in an inert gas, such as nitrogen or argon, or preferably in an oxidising gas, such as pure oxygen or a mixture of oxygen with an inert gas. According to the invention, treatment is preferably under vacuum at about 700°.

The rise in temperature is preferably gradual, its speed being, for example, between about 10° and about 500° C. per hour. The duration of the thermal pretreatment is, for example, from about 1 to about 12 hours. This treatment enables the elimination of the water contained in the silica. If the heating of the silica is done by means of the gaseous phase the flow rate of gas is regulated as a function of the temperature to be reached. At the end of the thermal pretreatment, the silica is cooled and shielded from moisture.

(d) Transformation of $Ni^{2+}$ ions into $Ni^+$

The silica obtained at the end of the thermal pretreatment is then subjected to a treatment by a trialkylphosphine or a trialkylphosphine precursor, and this treatment can be conducted at ambient temperature, in gaseous phase or in liquid phase. The amount of phosphine used is in excess with respect to the supported nickel. The trialkylphosphine/Ni ratio is advantageously comprised between about 3 and about 6. When the transformation is carried out in gaseous phase, the phosphine pressure is preferably between about 6650 and 13,500 Pa. The reduction may be followed and checked by EPR and visible-UV spectroscopy from the increase in the intensity of the signals of the $Ni^+$ $(palk_3)_4$ species formed, and lasts from 1 to 2 hours in the gaseous phase.

In liquid phase, this reduction is conducted in a solvent of the phosphines, for example toluene or heptane. The reduction is immediate in an solvent medium.

As trialkylphosphine precursor, it is possible to use for example, bis(dimethylphosphine)methane or bis(diethylphosphine)methane.

The EPR and visible UV characteristics of the $Ni^+(Palk_3)_4$ are as follows:

| alk | g ∥ | g ⊥ | A (gauss) ∥ | A (gauss) ⊥ | UV-vis nm |
|---|---|---|---|---|---|
| Eth | 2.27 | 2.065 | 40 | 50 | 1 400 |
| Me | 2.21 | 2.052 | 40 | 50 | 1 175 |

It is possible moreover to show that the reduction of the $Ni^{2+}$ ions into $Ni^+$ is complete by the disappearance of the characteristic bands of $Ni^{2+}$ in the accompanying visible UV spectra. In the spectra, the bands characteristics of $Ni^{2+}$ appear at about 700 nanometers.

(e) Activation of the catalyst resulting in the in the production of the active species of $Ni^+(Palk_3)_2$ and $Ni^+ (Palk_3)$ These species are obtained by treatment under vacuum of the preceding catalyst comprising $Ni^+(Palk_3)_4$ at a temperature which depends on the nature of the trialkylphosphine, preferably for 30 to 60 minutes.

Concerning tricyclohexylphosphine ligand, the process could be the same as the process described in EP No. 0089895. The obtained catalyst is purified by removal under vacuum to obtain $Ni^+(P(C_6H_{11})_3)$ substantially.

The temperatures at which the removal of the catalyst is performed as a function of the trialkylphosphine and of the number of trialkylphosphine ligands that are preserved in the co-ordination sphere of the $Ni^+$, are the following:

| | |
|---|---|
| $Ni^+(PEth_3)_2$ | 50 to 150° C. |
| $Ni^+(PMe_3)_2$ | 300 to 400° C. |
| $Ni^+(PEth_3)$ | 150 to 250° C. |

| | |
|---|---|
| $Ni^+(P(C_6H_{11})_3)$ | ambient temperature |

The invention also relates to a process of selective dimerisation of ethylene or propylene into monoolefines bringing into action a catalyst such as is previously defined. The dimerisation is carried out by contacting the ethylene or the propylene with the catalyst. The olefine may be used in gaseous phase or in liquid phase, in the pure state or in solution in a solvent. The best solvents for the reaction are paraffinic or aromatic hydrocarbons, or their chlorinated derivatives, such as pentane, heptane, benzene toluene, methylene chloride, dihchlorethane, chlorobenzene.

The dimerisation temperature is advantageously between about 0° and about 100° C., preferably between about 30° and about 40° C. and the pressure is selected to maintain a gaseous or liquid phase. Pressure may vary between $10^5$ and $50 \times 10^5$ Pa, preferably between about $20 \times 10^5$ Pa and about $30 \times 10^5$ Pa. The dimerisation may be conducted in a closed system (the catalyst and the olefine are introduced into the reactor at a single time), or in an open system (the olefine is passed through a bed of the catalyst), the best results being obtained in an open system. The contact time between the reactant and the catalyst is usually between about 1 minute and about 24 hours.

Preferably, the dimerisation of ethylene is performed on catalysts with active sites comprising one or two trialkylphosphine ligands, and 1-butene is then obtained selectively, and the dimerisation of propylene on catalysts whose active sites comprise a trialkylphosphine ligand, to obtain selectively monolefines.

Preferably, in the catalysts employed, the trialkylphosphines are triethylphosphines.

BRIEF DESCRIPTION OF THE DRAWINGS

In the drawings FIGS. 1 and 2 represent the spectra of the catalysts according to the invention in the case of reduction by $PMe_3$ (FIG. 1) and by $PEth_3$ (FIG. 2).

In FIG. 1: (1) corresponds to the un-reduced catalyst coming from step (c), (2) to the treated catalyst coming from step (d), (3) to the catalyst removed at 200° C., (4) to the catalyst removed at 300° for 15 min.

In FIG. 2: (1) corresponds to the un-reduced catalyst coming from (c), (2) to the treated catalyst coming from (d), (3) to the catalyst treated under vacuum at 150° for 30 minutes, (4) to the catalyst treated under vacuum at 250° C. for 35 min.

In these two Figures, the bands around 700 nm, indicated by an arrow, disappear in the course of steps (d) and (e) which shows total reduction of $Ni^{2+}$ into $Ni^+$.

FIGS. 3, 4, and 5 show the results of dimerisation of ethylene and of propylene and will be described more precisely in the Examples.

DESCRIPTION OF PREFERRED EMBODIMENTS

EXAMPLE 1

(steps a and b)

30 g of silica are treated at ambient temperature with 1 liter of aqueous ammonia solution at pH 11.6, with slight stirring for 24 hours. That the drop in the pH has remained less than 0.3 unit is verified. The silica used is: either a microporous silica (mean diameter of the pores 5 nm) or a spherosil (mean diameter of the pores 8 nm), the two silicas being marketed by the Rhône-Poulenc Company. After filtration, the samples so treated are then contacted at ambient temperature with 1 liter of a solution containing $Ni(NH_3)_6^{2+}$, ions obtained by dissolving 0.05 mole of nickel nitrate in an aqueous solution containing 0.3 mole of ammonium nitrate and 0.5 mole of ammonia and whose pH is close to 9.8. Stirring is continued for 60 hours at ambient temperature. The silica is filtered and then washed with deionized water, dried at 50° C. under vacuum. Elementary analysis shows that its nickel content is 1.7% by dry weight.

EXAMPLE 2

(steps a and b)

17 g of silica are treated with an aqueous solution of ammonia under the conditions described in the first step of Example 1. After filtration, the silica is placed in 1 liter of a solution containing $Ni(NH_3)_6^{2+}$ ion prepared from the solution of 0.1 mole of nickel nitrate and 0.6 mole of ammonium nitrate in an aqueous solution containing 4 moles of ammonia. The solution has a pH close to 10.4. After 60 hours of stirring at room temperature the silica is washed, filtered and dried as in Example 1. It titrates 4.2% of nickel for the RP microporous silica support in the form of extruded elements and 4.9% of nickel in the case of the Pechiney-St-Gobain spherosil support.

EXAMPLE 3

(step c)

The samples 1 or 2 as obtained in examples 1 or 2 are placed in a tube under vacuum and heated gradually to 700° C. The tube is then cooled to room temperature.

EXAMPLE 4

(steps d and e)

400 mg of samples 1 or 2 as obtained in Example 3 are transferred under vacuum into a volume of 50 cm, then treated for 2 hours at room temperature under a pressure of about 7 980 Pa of triethylphosphine. The samples are then evaporated under vacuum for 15 minutes at ambient temperature, then for 1 hour at 100° C. They are then cooled under vacuum to room temperature. In this way the $Ni(PEth_3)_2$ catalysts are obtained. These catalysts are preferably preserved under vacuum.

EXAMPLE 5

(steps d and e)

To obtain the catalysts with $Ni(PEth_3$, 400 mg of the samples of catalysts 1 or 2 are treated in the same manner as in Example 4 until evaporation under vacuum which is conducted for 15 minutes at ambient temperature, then 1 hours at 200° C. These catalysts are also preferably preserved under vacuum.

EXAMPLE 6

(steps d and e)

To form the $Ni(Me_3)_2$, catalysts the procedure is similar to that in Examples 4 and 5, starting from 400 mg of samples 1 or 2 obtained according to Example 3, by first treating under a pressure of about 7 980 Pa of triethylphosphine then by evacuating under vacuum for 15 minutes at ambient temperature, then 1 hour at 350° C. These catalysts are also preferably preserved under vacuum.

EXAMPLE 7

(steps e)

To form Ni(P($C_6H_{11}$))$_3$) catalysts, procedure is in the same manner as previously, the removal being carried out under vacuum over about 1 hour at ambient temperature.

EXAMPLE 8

Dimerisation of Ethylene into 1 Butene

This example was carried out under the dynamic procedure (open) on about 150 mg of catalyst. The accompanying table shows the results obtained for the catalysts according to the invention, in comparison with known Ni catalysts, under different experimental conditions. These results collected in Table 1 below show the much greater stability of the catalysts according to the invention, as well as an advantageous selectivity in 1-butene.

EXAMPLE 9

Other examples of dimerisation of ethylene into 1-butene have been carried out, whose results appear in the diagrams of FIGS. 3 and 4.

For a pressure of 20, $10^5$Pa, at 40° C., and at a conversion ratio of 5% in dynamic regime, the diagram of FIG. 3 shows the selectivity (%) (A), the molar percentage of 1-butene obtained (B) and the stability in hours (C), this for Ni$^+$(PEth$_3$), catalysts, that is to say known catalysts (n=0), in comparison with the catalysts according to the invention (n=1 and n=2), as well as catalysts where the co-ordination sphere comprises three triethylphosphine ligands (n=3). For a pressure of 20 ·$10^5$ Pa, at 25° C., in a reactor of 100 ml in static regime, for Ni$^+$(PEth$_3$)$_n$ catalysts (n=0, n=1 and n=2), the diagram of FIG. 4 shows the conversion ratio (A), the molar percentage of 1-butene obtained (B) and the dimer selectivity (C). From these results, it appears that the catalysts according to the invention (n=1 and n=2) are stable more than 24 h, contrary to the catalysts for which n equals 0 or 3.

In addition, at high conversion ratios, the selectivity of the dimer remains good for the catalysts according to the invention.

It emerges clearly from these results that the presence of two selective blocking ligands modifies considerably the selectivity of the catalyst according to the invention: the selectivity for the obtaining of 1-butene from ethylene is higher than 95% for a conversion of 25%.

EXAMPLE 10

Dimerisation of Propylene

With the catalysts according to the invention, the dimerisation of propylene, has also been performed for which the catalysts according to the invention are shown also to be much more stable than known catalysts.

In addition, they are reusable.

Thus, the diagram of FIG. 5 gives results of conversion (A) of selectivity in dimers of $C_6$(B) and of distribution of dimers obtained (C) for each of the catalysts indicated.

The dimerisation of the propylene was performed in static regime at atmospheric pressure and at a temperature of 25° C.

These results show that it is possible to obtain conversion ratios of the order of 50% in certain cases and show the effect of the number and the nature of the ligands on the conversion ratio.

EXAMPLE 11

The following table establishes the comparison between the reaction products of the dimerisation of propylene when a known catalyst is used, a catalyst containing a triethylphosphine or tricyclohexylphosphine ligand.

The experimental conditions are as follows:
reaction temperature: 40° C.
initial pressure: 5·10 Pa,
catalyst with 2.1% by weight of nickel,
25% conversion,
static regime.

TABLE II

| MOLE % | Ni$^+$ | Ni$^+$(PEth$_3$) | Ni$^+$(P($C_6H_{11}$)$_3$) |
|---|---|---|---|
| 1-hexane + 2 methyl-1-propene | 4.7 | 9 | 4.8 |
| transhexane + 2 methyl-2-pentene | 39.6 | 29.8 | 35.2 |
| Cis 2-hexene | 4.5 | 0.9 | 4.6 |
| 3-hexene | 4.2 | 0.2 | 3.7 |
| 4 methyl-1-pentene | 3.8 | 1.5 | 5.1 |
| 2,3-dimethyl-1-butene + 4 methyl-2 pentene cis | 9 | 25.9 | 13.4 |
| 4 methyl-2-pentene trans | 27 | 22 | 27 |
| 2,3 dimethyl-2-butene | 6.7 | 9.4 | 6.2 |

EXAMPLE 12

TABLE I

| Catalyst | P in Pa | T° C. | Flow Rate 1h$^{-1}$ | Conversion mole $C_2H_4$ % | molar rotation number $C_2H_4Ni^{-1}h^{-1}$ | Stability y | Selectivity of dimers % | Distribution of $C_4$ mole % | |
|---|---|---|---|---|---|---|---|---|---|
| | | | | | | | | 1 butene | 2 butene |
| Ni$^+$ | 20 · $10^5$ | 40 | 12 | 10 | 317 | 3 | 88 | 71 | 29 |
| Ni$^+$ | 20 · $10^5$ | 40 | 3 | 37 | 277 | 3 | 82 | 51 | 49 |
| Ni$^+$(PEth$_3$)$_2$ | 20 · $10^5$ | 40 | 3 | 5.5 | 63.7 | >24 | 80 | 94 | 6 |
| Ni$^+$(PEth$_3$) | 20 · $10^5$ | 40 | 3 | 5.3 | 32.3 | >24 | 84 | 93 | 7 |
| Ni$^+$(PEth$_3$)$_2$ | 20 · $10^5$ | 40 | 1.3 | 9.1 | 45 | >24 | 83 | 95 | 5 |

Dimerisation of Propylene

The selectivity in $C_6$ dimer in static regime under the same conditions of temperature and pressure has also been compared, at a conversion ratio of 50% and for the usual Ni$^+$ catalysts and the Ni$^+$(P($C_6H_{11}$)$_3$) catalysts. The selectivity in $C_6$ dimer passes from 30% in the absence of phosphine to 53% in the presence of tricyclohexylphosphine.

We claim:

1. A catalyst for the selective dimerization of ethylene or propylene into monoolefines, comprising nickel on a silica support, whose active sites are complexes of the Ni$^+$ ion wherein substantially all of the nickel is present in the form of Ni$^+$ complexes co-ordinated with the oxygen of the surface of the silica support and whose coordination sphere comprises 1 or 2 trialkylphosphine ligands, said catalyst having been prepared by the following different successive steps:

(a) treating silica with an aqueous solution of a compound generating monovalent cations, at a pH higher than about 10, so as to fix at least a part of said monovalent cations to the silica;

(b) treating the silica thus obtained with an aqueous solution of a divalent nickel salt and a complexing agent for the nickel salt at a pH at least equal to about 8, to exchange competitively said monovalent cations borne by the silica with divalent nickel cations;

(c) bringing the so-modified silica to a temperature between about 300° and about 900° C.;

(d) treating the so-obtained silica with a trialkylphosphine or one of its precursors in excess for a time at least sufficient for the production of complexes of the $Ni^+$ co-ordinated with four trialkylphosphine ligands; and, (e) treating the resulting silica under vacuum at a suitable temperature and for an appropriate time to obtain active Ni sites whose co-ordination sphere comprises at the most two trialkylphosphine ligands.

2. Catalyst according to claim 1, wherein one or more ligands are selected from among trimethylphosphine, triethylphosphine and tricyclohexylphosphine.

3. Catalyst according to claim 1, containing about 1% to about 6% of $Ni^+$ by dry weight.

4. Catalyst according to claim 1, wherein the $Ni^+$ co-ordination sphere comprises two triethylphosphine ligands, the catalyst then having the following characteristics:
in EPR:

| factors | $g\| = 2.32$ | and $g\bot = 2.083$ |
|---|---|---|
| hyperfine tensors | $A_1 = 62\ G$ | and $A_2 = 85\ G$ | and,
in UV: transitions at 465 nm and 330 nm.

5. Catalyst according to claim 1, wherein the $Ni^+$ co-ordination sphere comprises two trimethylphosphine ligands, the catalyst then having the following characteristics:
in EPR:

| factors | $g\| = 2.26$ | and $g\bot = 2.077$ |
|---|---|---|
| hyperfine tensors | $A_1 = 60\ G$ | and $A_2 = 75\ G$ | and,
in UV: transition at 450 nm and 327 nm.

6. Catalyst according to claim 1, wherein the Ni co-ordination sphere comprises a triethylphosphine ligand, the catalyst then having the following characteristics:
in EPR:

| factors | $g\| = 2.013$ | and $g\bot = 2.125$ |
|---|---|---|
| hyperfine tensors | $A_1 = 70\ G$ | | and,
in UV: transition at 400 nm.

7. Catalyst according to claim 1, wherein the co-ordination sphere of the Ni comprises a trimethylphosphine ligand, the catalyst having then the following characteristics:
in EPR:

| factors | $g\| = 2.015$ | and $G\bot = 2.120$ |
|---|---|---|
| hyperfine tensors | $A\bot = 55\ G$ | | and,
in UV: transition at 400 nm.

8. Catalyst according to claim 1, wherein the co-ordination sphere of the Ni comprises a tricyclohexylphosphine ligand, the catalyst then having the following characteristics:
in EPR:

| factors | $g\| = 2.017$ | and $g\bot = 2.12$ |
|---|---|---|
| hyperfine tensors | $A\bot = 55\ G$ | |

9. Process for the manufacture of a catalyst comprising nickel on a silica support, whose active sites are complexes of the $Ni^+$ ion, wherein practically all of the nickel is present in the form of $Ni^+$ complexes co-ordinated with the oxygen of the surface of the silica support and whose co-ordination sphere comprises 1 or 2 trialkylphosphine ligands, said process comprising the following different successive steps:

(a) treating silica with an aqueous solution of a compound generating monovalent cations, at a pH higher than about 10, so as to fix at least a part of said monovalent cations to the silica;

(b) treating the silica thus obtained with an aqueous solution of a divalent nickel salt and a complexing agent for the nickel salt at a pH at least equal to about 8, to exchange competitively said monovalent cations borne by the silica with divalent nickel cations;

(c) bringing the so-modified silica to a temperature between about 300° and about 900° C.;

(d) treating the so-obtained silica with a trialkylphosphine or one of its precursors in excess for a time at least sufficient for the production of complexes of the $Ni^+$ co-ordinated with four trialkylphosphine ligands; and (e) treating the resulting silica under vacuum at a suitable temperature and for an appropriate time to obtain active Ni sites whose co-ordination sphere comprises at the most two trialkylphosphine ligands.

10. Process according to claim 9, wherein step (c) is performed at about 700° C.

11. Process according to claim 9, wherein step (c) is performed under vacuum.

12. Process according to claim 9, wherein at step (d), the silica is treated with a trimethylphosphine a triethylphosphine, bis(dimethylphosphine)methane or bis(diethylphosphine)methane.

13. Process according to claim 9, wherein at step (d) the excess reactant used corresponds to a trialkylphosphine/Ni ratio ranging from about 3 to about 6.

14. Process according to claim 9, wherein at step (d) the silica is treated in liquid phase in a solvent for trialkylphosphines, or in gaseous phase, and at ambient temperature.

15. Process according to claim 14, wherein at step (d) the solvent is toluene or heptane.

16. Process according to claim 9, wherein at step (d) the pressure of phosphine is of the order of 6,650 to 13,500 Pa.

17. Process according to claim 9, wherein step (e) is performed between about 50° and 250° C., for a time ranging from about 30 min. to about 1 hour to obtain active $Ni^+$, sites whose co-ordination sphere comprises one or two triethylphosphine ligands.

18. Process according to claim 9, wherein step (e) is performed between about 300° and 400° C. for a time ranging from about 30 min. to about 1 hour to obtain active $Ni^+$ sites whose co-ordination sphere comprises two trimethylphosphine ligands.

19. The process of claim 9 wherein step (d) is carried out for one to two hours in the gaseous phase.

20. A process for the dimerization of ethylene, wherein said process is performed in the presence of a catalyst comprising nickel on a silica support, whose active sites are complexes of the $Ni^+$ ion, wherein practically the whole of the nickel is present in the form of $Ni^+$ complexes co-ordinated with the oxygen of the surface of the silica support and the active $Ni^+$ sites contain one or two trialkylphosphine ligands, said catalyst having been prepared by the following different successive steps:

(a) treating silica with an aqueous solution of a compound generating monovalent cations, at a pH higher than about 10, so as to fix at least a part of said monovalent cations to the silica;

(b) treating the silica thus obtained with an aqueous solution of a divalent nickel salt and a complexing agent for the nickel salt at a pH at least equal to about 8, to exchange competitively said monovalent cations borne by the silica with divalent nickel cations;

(c) bringing the so-modified silica to a temperature between about 300° and about 900° C.;

(d) treating the so-obtained silica with a trialkylphosphine or one of its precursors in excess for a time at least sufficient for the production of complexes of the $Ni^+$ co-ordinated with four trialkylphosphine ligands; and, (e) treating the resulting silica under vacuum at a suitable temperature and for an appropriate time to obtain active Ni sites whose co-ordination sphere comprises at the most two trialkylphosphine ligands.

21. The process of claim 20 wherein said trialkylphosphine ligands are triethylphosphine ligands.

22. A process in accordance with claim 20 wherein the active $Ni^+$ sites contain one trialkylphosphine ligand.

23. The process of claim 22 wherein said trialkylphosphine ligand is a triethylphosphine ligand.

* * * * *